US012765826B2

(12) United States Patent
Huang et al.

(10) Patent No.: US 12,765,826 B2
(45) Date of Patent: Oct. 20, 2026

(54) ECG ELECTRODE, FABRICATION METHOD THEREOF, AND ELECTRONIC DEVICE

(71) Applicant: Huawei Technologies Co., Ltd., Shenzhen (CN)

(72) Inventors: Yujian Huang, Shenzhen (CN); Qiu Jin, Shenzhen (CN); Ming Cai, Dongguan (CN); Longyu Li, Dongguan (CN)

(73) Assignee: HUAWEI TECHNOLOGIES CO., LTD., Shenzhen (CN)

( * ) Notice: Subject to any disclaimer, the term of this patent is extended or adjusted under 35 U.S.C. 154(b) by 283 days.

(21) Appl. No.: 18/514,111

(22) Filed: Nov. 20, 2023

(65) Prior Publication Data

US 2024/0081710 A1 Mar. 14, 2024

Related U.S. Application Data

(63) Continuation of application No. PCT/CN2022/094008, filed on May 20, 2022.

(30) Foreign Application Priority Data

May 21, 2021 (CN) ........................ 202110560688.9

(51) Int. Cl.
*A61B 5/263* (2021.01)
*A61B 5/28* (2021.01)
(Continued)

(52) U.S. Cl.
CPC ................ *A61B 5/263* (2021.01); *A61B 5/28* (2021.01); *C23C 14/0605* (2013.01); (Continued)

(58) Field of Classification Search
CPC ......... A61B 5/259; A61B 5/261; A61B 5/263; A61B 5/266; A61B 5/268; A61B 5/282; (Continued)

(56) References Cited

U.S. PATENT DOCUMENTS

2016/0066852 A1* 3/2016 Cheng .................. A61B 5/6831 600/390

FOREIGN PATENT DOCUMENTS

CN 101444985 A 6/2009
CN 105644059 A 6/2016
(Continued)

OTHER PUBLICATIONS

Di Zhang et al, "Amorphous carbon films doped with silver and chromium to achieve ultra-low interfacial electrical resistance and long-term durability in the application of proton exchange membrane fuel cells", Jan. 20, 2019, XP085669921, total 12 pages.

*Primary Examiner* — Eun Hwa Kim
(74) *Attorney, Agent, or Firm* — Conley Rose, P.C.

(57) ABSTRACT

An electrocardiography (ECG) electrode includes an electrode substrate and a doped graphite-like carbon (GLC) film located on an outer surface of the electrode substrate. The doped GLC film includes GLC, and first nano-crystals and second nano-crystals that are embedded in the GLC. The first nano-crystal includes a weak carbon-bonding element. The weak carbon-bonding element has a part that exists in a form of a metallic elementary substance. The first nano-crystal includes a columnar structure. The columnar structure extends in a thickness direction of the doped GLC film. The second nano-crystal includes a strong carbon-bonding element. The strong carbon-bonding element bonds with the carbon element in the GLC through a chemical bond. The second nano-crystals are distributed between adjacent and spaced columnar structures.

20 Claims, 2 Drawing Sheets

(51) Int. Cl.
*C23C 14/06* (2006.01)
*C23C 14/34* (2006.01)

(52) U.S. Cl.
CPC ...... *C23C 14/34* (2013.01); *A61B 2562/0285* (2013.01); *A61B 2562/125* (2013.01)

(58) Field of Classification Search
CPC .............. C23C 14/0605; C23C 14/024; C23C 14/3464; C23C 14/3492; C23C 14/022
See application file for complete search history.

(56) References Cited

FOREIGN PATENT DOCUMENTS

| | | | |
|---|---|---|---|
| CN | 106282918 | A | 1/2017 |
| CN | 107326336 | A | 11/2017 |
| CN | 107881466 | A | 4/2018 |
| CN | 109055910 | A | 12/2018 |
| CN | 110507316 | A | 11/2019 |
| CN | 110578114 | A | 12/2019 |
| CN | 110643943 | A | 1/2020 |
| CN | 111593316 | A | 8/2020 |
| CN | 113991134 | A | 1/2022 |
| CN | 115251933 | A | 11/2022 |

* cited by examiner

ECG ELECTRODE, FABRICATION METHOD THEREOF, AND ELECTRONIC DEVICE

CROSS-REFERENCE TO RELATED APPLICATIONS

This is a continuation of International Patent Application No. PCT/CN2022/094008 filed on May 20, 2022, which claims priority to Chinese Patent Application No. 202110560688.9 filed on May 21, 2021. The disclosures of the aforementioned applications are hereby incorporated by reference in their entireties.

TECHNICAL FIELD

This application relates to the field of material technologies, and more specifically, to an electrocardiography (ECG) electrode, a fabrication method thereof, and an electronic device.

BACKGROUND

Currently, electronic devices such as a smartwatch and a smart band keep developing. These smart electronic devices usually include an ECG electrode. The ECG electrode is at a location that is on a housing of the smart electronic device and that is in contact with skin, and is configured to monitor the heart of a person (or referred to as a "monitored object") wearing the smart terminal device. Stainless steel or titanium alloy is usually used as a substrate material of the ECG electrode. Both stainless steel and titanium alloy have defects of low hardness and poor wear resistance. As a result, with long-term use of the electronic device, the ECG electrode may be worn out or even become invalid, to disable the electronic device to monitor an electrocardiogram any longer.

SUMMARY

This disclosure provides an ECG electrode. An outer surface of an electrode substrate of the ECG electrode is plated with a doped graphite-like carbon film, so that the ECG electrode has excellent conductivity, and also has high hardness and high wear resistance. In addition, this disclosure further provides a fabrication method for the ECG electrode and an electronic device using the ECG electrode.

According to a first aspect, an embodiment of this disclosure provides an ECG electrode, including an electrode substrate and a doped graphite-like carbon film located on an outer surface of the electrode substrate. The doped graphite-like carbon film includes graphite-like carbon, and first nano-crystals and second nano-crystals that are doped in the graphite-like carbon. The graphite-like carbon includes a carbon element. The graphite-like carbon has an amorphous carbon structure. The first nano-crystal includes a weak carbon-bonding element. The weak carbon-bonding element has a part that exists in a form of a metallic elementary substance. The first nano-crystal includes a columnar structure. The columnar structure extends in a thickness direction of the doped graphite-like carbon film. The second nano-crystal includes a strong carbon-bonding element. The strong carbon-bonding element bonds with the carbon element in the graphite-like carbon through a chemical bond. The second nano-crystals are distributed between adjacent and spaced columnar structures.

In the foregoing technical solution, the graphite-like carbon (GLC) has advantages of high hardness and good wear resistance, but has poor conductivity in a thickness direction. The first nano-crystal of the columnar structure is embedded in the amorphous carbon structure of the graphite-like carbon, to enhance the conductivity of the graphite-like carbon in the thickness direction of the graphite-like carbon. However, in addition, introduction of the first nano-crystal reduces density and hardness inside the graphite-like carbon, so that the hardness and the wear resistance of the graphite-like carbon are reduced. The second nano-crystal is introduced in the amorphous carbon structure of the graphite-like carbon and the columnar structure of the first nano-crystal, to enhance strength and wear resistance of the doped graphite-like carbon film.

With reference to the first aspect, in a first possible implementation of the first aspect, the weak carbon-bonding element includes one or more of the following materials: Cu, Ag, Au, and Al. In the foregoing technical solution, the weak carbon-bonding element is difficult to chemically bond with the carbon element, and mainly exists in the form of the metallic elementary substance in the graphite-like carbon. The metals Cu, Ag, Au, and Al have excellent conductivity, so that the formed first nano-crystal is embedded in the amorphous carbon structure of the graphite-like carbon, to enhance the conductivity of the graphite-like carbon.

With reference to the first aspect or the first possible implementation of the first aspect, in a second possible implementation of the first aspect, the doped graphite-like carbon film includes a first surface facing the electrode substrate and a second surface opposite to the first surface. An atomic percentage of the weak carbon-bonding element gradually increases in a thickness direction from the first surface to the second surface. In the foregoing technical solution, as the atomic percentage of the weak carbon-bonding element increases, the first nano-crystal is precipitated in the columnar structure. The first nano-crystal of the columnar structure is also referred to as a columnar nano-crystal. The columnar nano-crystal including the weak carbon-bonding elements Cu, Ag, Au, and Al has excellent conductivity, and may form a longitudinal conductive channel in the graphite-like carbon, so that the conductivity of the graphite-like carbon in the thickness direction of the graphite-like carbon is enhanced, and high ECG signal quality is achieved.

With reference to the first aspect or any one of the first to the second possible implementations of the first aspect, in a third possible implementation of the first aspect, the doped graphite-like carbon film includes the first surface facing the electrode substrate and the second surface opposite to the first surface. A first nano-crystal close to the first surface is of a cluster structure. A first nano-crystal close to the second surface is of a columnar structure. In the foregoing technical solution, an atomic percentage of a weak carbon-bonding element close to the first surface is low, and a first nano-crystal formed from the weak carbon-bonding element is precipitated in a cluster structure. An atomic percentage of a weak carbon-bonding element closer to the second surface is greater, and a first nano-crystal formed from the weak carbon-bonding element is precipitated in a columnar structure.

With reference to the third possible implementation of the first aspect, in a fourth possible implementation of the first aspect, the second nano-crystals are distributed between a plurality of cluster structures and a plurality of columnar structures. In the foregoing technical solution, a distribution manner of the second nano-crystals and the first nano-crystals helps enhance bonding force inside the doped graphite-like carbon film. In addition, because the second nano-crystal is a hard carbide, embedding the second nano-crystals between the cluster structures and the columnar structures of the first nano-crystals helps better enhance the hardness of the entire doped graphite-like carbon film.

With reference to the first aspect or any one of the first to the fourth possible implementations of the first aspect, in a fifth possible implementation of the first aspect, the strong carbon-bonding element includes one or more of the following materials: Cr, W, and Ti. The strong carbon-bonding element bonds with the carbon element in the graphite-like carbon through the chemical bond, to generate second nano-crystals CrC, WC, and TiC. The foregoing three carbides are all hard carbides, and have advantages of high hardness and high wear resistance. The second nano-crystal is embedded in the amorphous carbon structure of the graphite-like carbon, to improve the hardness of the doped graphite-like carbon film and enhance the wear resistance of the doped graphite-like carbon film.

With reference to the first aspect or any one of the first to the fifth possible implementations of the first aspect, in a sixth possible implementation of the first aspect, the doped graphite-like carbon film includes the first surface facing the electrode substrate and the second surface opposite to the first surface. An atomic percentage of the strong carbon-bonding element gradually decreases in the thickness direction from the first surface to the second surface. In the foregoing technical solution, a great atomic percentage of the weak carbon-bonding element may be maintained close to the second surface, so that the doped graphite-like carbon film maintains high electrical signal quality close to the second surface. In addition, from the first surface to the second surface, the atomic percentage of the strong carbon-bonding element gradually decreases, and the atomic percentage of the weak carbon-bonding element gradually increases. Such a complementary design helps improve bonding force of the doped graphite-like carbon film.

With reference to the first aspect or any one of the first to the sixth possible implementations of the first aspect, in a seventh possible implementation of the first aspect, the ECG electrode further includes a transition layer, and the transition layer is located between the electrode substrate and the doped graphite-like carbon film. In the foregoing technical solution, atoms may be diffused between the transition layer and the electrode substrate and between the transition layer and the doped graphite-like carbon film, to improve bonding force between the electrode substrate and the doped graphite-like carbon film.

With reference to the seventh implementation of the first aspect, in an eighth possible implementation of the first aspect, the transition layer includes one or more of the following materials: Cr, W, and Ti. The transition layer is made of a same material as the strong carbon-bonding element in the doped graphite-like carbon film, to further improve bonding force between the transition layer and the doped graphite-like carbon film.

According to a second aspect, an embodiment of this disclosure further provides an electronic device, including a processor and the ECG electrode according to any one of the foregoing implementations. The ECG electrode is configured to be in contact with skin of a monitored object to obtain an electrocardiography signal of the monitored object, and transmit the electrocardiography signal to the processor. The processor is configured to process the electrocardiography signal. For effects achievable by the electronic device provided in the second aspect of this disclosure, refer to the effects corresponding to the first aspect and various implementation solutions of the first aspect. Details are not described herein again.

According to a third aspect, an embodiment of this disclosure further provides a fabrication method for an ECG electrode based on the first aspect. A transition layer is sputtered on the outer surface of the electrode substrate. The doped graphite-like carbon film is sputtered on a surface, away from the electrode substrate, of the transition layer. The doped graphite-like carbon film includes the graphite-like carbon, and the first nano-crystals and the second nano-crystals that are embedded in the graphite-like carbon. The graphite-like carbon includes the carbon element. The graphite-like carbon has the amorphous carbon structure. The first nano-crystal includes the weak carbon-bonding element. The weak carbon-bonding element has the part that exists in the form of the metallic elementary substance. The first nano-crystal includes the columnar structure. The columnar structure extends in the thickness direction of the doped graphite-like carbon film. The second nano-crystal includes the strong carbon-bonding element. The strong carbon-bonding element bonds with the carbon element in the graphite-like carbon through the chemical bond. The second nano-crystals are distributed between adjacent and spaced columnar structures. In the foregoing technical solution, the first nano-crystal of the columnar structure is embedded in the amorphous carbon structure of the graphite-like carbon, to enhance the conductivity of the graphite-like carbon in the thickness direction of the graphite-like carbon. In addition, the second nano-crystal is introduced in the amorphous carbon structure of the graphite-like carbon and the columnar structure of the first nano-crystal, to enhance the strength and the wear resistance of the doped graphite-like carbon film. In addition, the electrode substrate may be plated in a physical vapor deposition (PVD) manner, and fabricating the doped graphite-like carbon film through PVD is easy to operate and control and convenient to promote and use.

With reference to the third aspect, in a first possible implementation of the third aspect, the weak carbon-bonding element includes one or more of the following materials: Cu, Ag, Au, and Al. The doped graphite-like carbon film includes a first surface facing the electrode substrate and a second surface opposite to the first surface. An atomic percentage of the weak carbon-bonding element gradually increases in a thickness direction from the first surface to the second surface. A first nano-crystal close to the first surface is of a cluster structure. A first nano-crystal close to the second surface is of a columnar structure. In the foregoing technical solution, a columnar nano-crystal including the weak carbon-bonding elements Cu, Ag, Au, and Al has excellent conductivity, and may form a longitudinal conductive channel in the graphite-like carbon, so that the conductivity of the graphite-like carbon in the thickness direction of the graphite-like carbon is enhanced, and high ECG signal quality is achieved.

With reference to the first possible implementation of the third aspect, in a second possible implementation of the third aspect, the strong carbon-bonding element includes one or more of the following materials: Cr, W, and Ti. The doped graphite-like carbon film includes the first surface facing the electrode substrate and the second surface opposite to the first surface. An atomic percentage of the strong carbon-bonding element gradually decreases in the thickness direction from the first surface to the second surface. The second nano-crystals are distributed between a plurality of cluster structures and a plurality of columnar structures. In the foregoing technical solution, the strong carbon-bonding elements Cr, W, and Ti bond with the carbon element in the graphite-like carbon through chemical bonds, to generate second nano-crystals CrC, WC, and TiC. The foregoing three carbides are all hard carbides, and have advantages of high hardness and high wear resistance. The second nano-crystal is embedded in the amorphous carbon structure of the graphite-like carbon, to improve the hardness of the doped graphite-like carbon film and enhance the wear resistance of the doped graphite-like carbon film. In addition, the atomic percentage of the strong carbon-bonding element gradually decreases in the thickness direction from the first surface to the second surface. In this way, a great atomic percentage of the weak carbon-bonding element may be maintained close to the second surface, so that the doped graphite-like carbon film maintains high electrical signal quality close to the second surface. In addition, from the first surface to the second surface, the atomic percentage of the strong carbon-bonding element gradually decreases, and the atomic percentage of the weak carbon-bonding element gradually increases. Such a complementary design helps improve bonding force of the doped graphite-like carbon film.

With reference to the third aspect or any one of the first to the second possible implementations of the third aspect, in a third possible implementation of the third aspect, the transition layer includes one or more of the following materials: Cr, W, and Ti. In the foregoing technical solution, atoms may be diffused between the transition layer and the electrode substrate and between the transition layer and the doped graphite-like carbon film, to improve bonding force between the electrode substrate and the doped graphite-like carbon film.

With reference to the third aspect or any one of the first to the third possible implementations of the third aspect, in a fourth possible implementation of the third aspect, a thickness of the transition layer is greater than or equal to 0.2 m and less than or equal to 0.6 m, and a thickness of the doped graphite-like carbon film is greater than or equal to 1.0 m and less than or equal to 1.4 m. In the foregoing technical solution, the thicknesses of the transition layer and the doped graphite-like carbon film are moderate, so that the ECG electrode may have a longer service life while ensuring high electrocardiography signal quality. Therefore, user experience is enhanced.

BRIEF DESCRIPTION OF DRAWINGS

To describe the technical solutions in embodiments of this disclosure more clearly, the following briefly describes embodiments. The accompanying drawings in the following description show some embodiments of this disclosure, and persons skilled in the art may derive other drawings from these accompanying drawings without creative efforts.

DESCRIPTION OF EMBODIMENTS

To make objectives, technical solutions, and effects of embodiments of this disclosure clearer, the following clearly describes the technical solutions in embodiments of this disclosure with reference to specific embodiments. The described embodiments are some but not all embodiments of this disclosure. All other embodiments obtained by persons skilled in the art based on embodiments of this disclosure without creative efforts shall fall within the protection scope of this disclosure.

The following describes specific embodiments of this disclosure with reference to the accompanying drawings.

Figure 1:
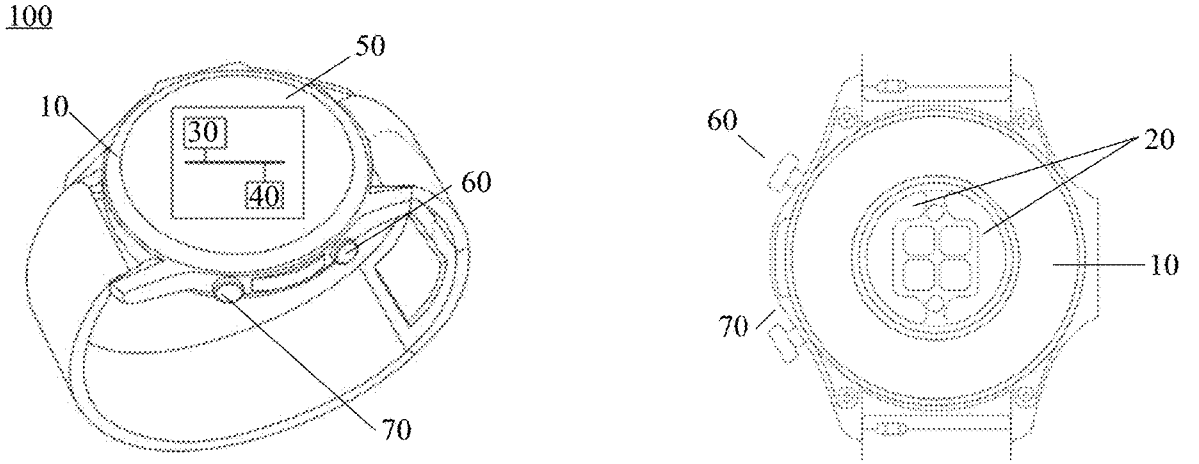
FIG. 1 is a schematic diagram of a structure of an electronic device 100 according to an embodiment of this disclosure.

FIG. 1 is a schematic diagram of a structure of an electronic device 100 according to an embodiment of this disclosure. The electronic device 100 has an electrocardiographic monitoring function. Specifically, the electronic device 100 may be an electronic product such as a mobile phone, a palmtop computer (personal digital assistant (PDA)), a notebook computer, or a wearable device. The wearable device may be a smartwatch, a smart band, smart glasses, a headset, or the like. In this embodiment of this disclosure, an example in which the electronic device 100 is a smartwatch is used for description.

In some embodiments, the electronic device 100 includes a housing 10, an ECG electrode 20, and a processor 30. The housing 10 is configured to accommodate and protect internal components (a movement, a watch face, a watch hand, and the like) of the electronic device 100. The housing 10 may be a rear housing of the electronic device 100, that is, a part of a housing that is in contact with skin of a user when the user wears the electronic device 100, or may be a complete housing. This is not limited in this embodiment of this disclosure. A material of the housing 10 may be insulating ceramic, for example, zirconium dioxide ($ZrO_2$) ceramic. The ECG electrode 20 may be embedded in a location that is on the housing 10 and that is in contact with the skin of the user. For example, the ECG electrode 20 may be located on the rear housing of the electronic device 100. When the user wears the electronic device 100, the ECG electrode 20 is in contact with the skin of the user. The ECG electrode 20 is configured to be in contact with skin of a monitored object to collect an electrocardiography signal of the monitored object. In this embodiment of this disclosure, the ECG electrode 20 may be in a ring shape, a multi-segment ring shape (for example, a two-segment ring shape or a four-segment ring shape), or the like. The ECG electrode 20 may alternatively be obtained through profiling design based on a product shape, a wall thickness, and other features of the electronic device 100. The processor 30 is mounted to an inner side of the housing 10. The processor 30 is in communication connection to the ECG electrode 20. The processor 30 is configured to obtain the electrocardiography signal from the ECG electrode 20, and process the electrocardiography signal, specifically, for example, perform filtering, amplification, and analog-to-digital conversion on the collected electrocardiography signal, to finally generate electrocardiographic data.

In some embodiments, the electronic device 100 further includes a memory 40. The memory 40 is located inside the housing 10, and is in communication connection to the processor 30. The memory 40 is configured to store a software program or code. The processor 30 processes the electrocardiography signal by executing the software program or the code.

In some embodiments, the electronic device 100 further includes a display screen 50. The display screen 50 is fastened to the housing 10. The display screen 50 is electrically connected to the processor 30, and is configured to display the electrocardiographic data obtained through processing. The user may learn of the electrocardiographic data of the user by viewing a pattern (for example, an electrocardiographic waveform) displayed on the display screen 50. The display screen 50 may be a touch display screen.

In some embodiments, the electronic device 100 may further include a crown 60 and a button 70. The crown 60 and the button 70 may be disposed on a front-housing component. The front-housing component is included in the housing 10. Both the crown 60 and the button 70 may perform some functions in response to an operation of the user. For example, the crown 60 is configured for date and time adjustment and winding. The button 70 may display a home screen in response to a pressing operation performed by the user with a finger. For example, the ECG electrode 20 may alternatively be located on an outer side of the crown 60 or an outer side of the button 70. The user may contact the crown 60 or the button 70 with a finger or another body part, so that the ECG electrode 20 collects the electrocardiography signal.

In this embodiment, because the electronic device 100 is small and convenient to carry, the user may wear the electronic device 100 at any time to measure real-time electrocardiographic data of the user in time by using the ECG electrode 20, to detect a health status in time.

Figure 2:
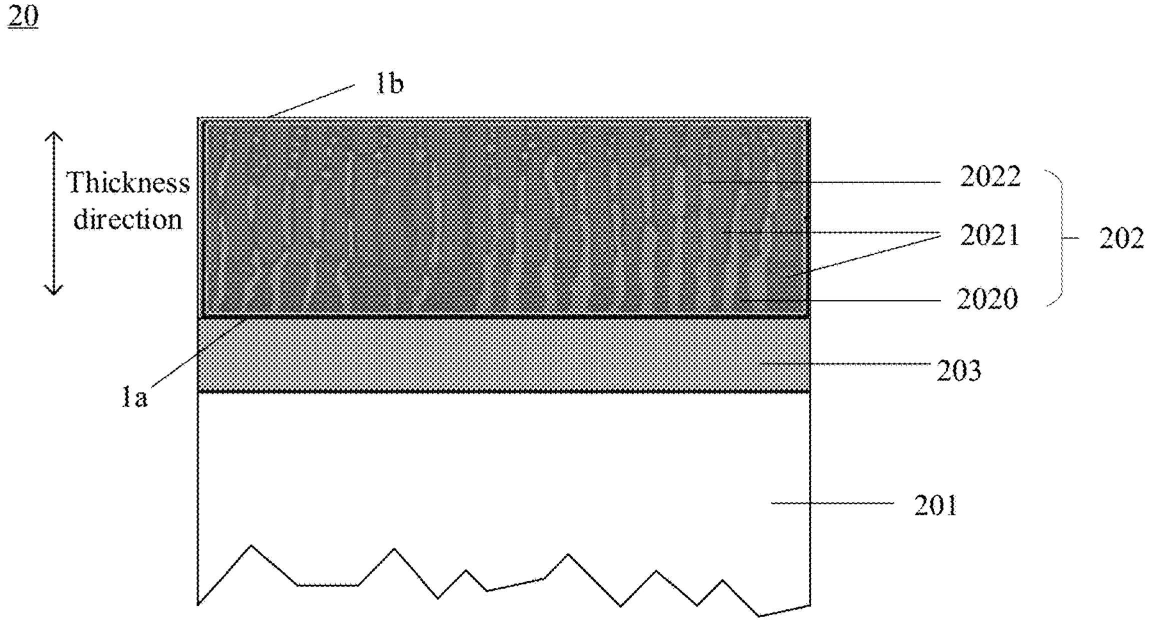
FIG. 2 is a schematic diagram of a structure of an ECG electrode 20 according to an embodiment of this disclosure.

FIG. 2 is a schematic diagram of a film layer structure of the ECG electrode 20. In some embodiments, the ECG electrode 20 includes an electrode substrate 201 and a conductive film layer formed on the electrode substrate 201. When the electronic device 100 is used, the conductive film layer is close to the skin of the user relative to the electrode substrate 201. The ECG electrode 20 not only needs to have conductivity, but also needs to have high hardness and high wear resistance, to meet use performance of the electronic device 100 in electrocardiographic monitoring.

An embodiment of this disclosure provides an ECG electrode 20. The ECG electrode 20 includes an electrode substrate 201, and further includes a doped graphite-like carbon film 202 located on an outer surface of the electrode substrate 201. The doped graphite-like carbon film 202 includes graphite-like carbon 2020, and first nano-crystals 2021 and second nano-crystals 2022 that are embedded in the graphite-like carbon 2020. In addition, the doped graphite-like carbon film 202 includes a first surface 1*a* facing the electrode substrate 201 and a second surface 1*b* opposite to the first surface 1*a*. Planes on which the first surface 1*a* and the second surface 1*b* are located are both approximately perpendicular to a thickness direction of the doped graphite-like carbon film 202.

In an embodiment, the electrode substrate 201 may be made of stainless steel, titanium alloy, aluminum alloy, or tungsten steel. The electrode substrate 201 has good conductivity and a light weight, which is conducive to transmitting an electrical signal and may implement lightweight products.

The GLC 2020 includes a carbon element. The graphite-like carbon 2020 has an amorphous carbon structure. The amorphous carbon structure is a structure in which carbon atoms in the graphite-like carbon 2020 are not arranged regularly and periodically, the carbon atoms are arranged irregularly in general, but adjacent carbon atoms are arranged regularly. The graphite-like carbon 2020 has advantages of high hardness and good wear resistance, but has poor longitudinal conductivity. The longitudinal conductivity is conductivity in a thickness direction of the graphite-like carbon 2020. The thickness direction of the graphite-like carbon 2020 is equivalent to the thickness direction of the doped graphite-like carbon film 202. The graphite-like carbon 2020 has poor longitudinal conductivity because the amorphous carbon structure of the graphite-like carbon 2020 includes a large quantity of laminated planar structures, and the laminated planar structures are parallel to each other and are perpendicular to the thickness direction of the graphite-like carbon 2020. Because electrons cannot freely move between layers, resistivity in a direction perpendicular to the laminated planar structure, that is, in the thickness direction of the graphite-like carbon 2020, is high, which is reflected as poor conductivity of the graphite-like carbon 2020 in the thickness direction of the graphite-like carbon 2020.

In an embodiment, the first nano-crystal 2021 is embedded in the amorphous carbon structure of the graphite-like carbon 2020, so that the conductivity of the graphite-like carbon 2020 in the thickness direction of the GLC 2020 may be enhanced. Specifically, the first nano-crystal 2021 includes a weak carbon-bonding element. The weak carbon-bonding element is an element that has weak affinity with the carbon element and that is difficult to chemically bond with the carbon element to form a carbide. For example, the weak carbon-bonding element may be Cu, Ag, Au, or Al. The first nano-crystal 2021 includes at least one weak carbon-bonding element, that is, the first nano-crystal 2021 may include only the weak carbon-bonding element Cu, Ag, Au, or Al, or may include any combination of two or more of the foregoing weak carbon-bonding elements.

The weak carbon-bonding element is difficult to chemically bond with the carbon element, and mainly exists in a form of a metallic elementary substance in the amorphous carbon structure. The metals Cu, Ag, Au, and Al have high conductivity, so that the formed first nano-crystal 2021 is embedded in the amorphous carbon structure of the graphite-like carbon 2020, to enhance the conductivity of the graphite-like carbon 2020.

Further, an atomic percentage of the weak carbon-bonding element may be controlled to gradually increase in a thickness direction from the first surface 1*a* to the second surface 1*b*, to enhance the conductivity of the graphite-like carbon 2020 in the thickness direction of the graphite-like carbon 2020. As the atomic percentage of the weak carbon-bonding element increases, the first nano-crystal 2021 is precipitated in a columnar structure. The columnar structure extends from the first surface 1*a* to the second surface 1*b*. The first nano-crystal 2021 of the columnar structure is also referred to as a columnar nano-crystal. The columnar nano-crystal including the weak carbon-bonding elements Cu, Ag, Au, and Al has excellent conductivity, and may form a longitudinal conductive channel in the graphite-like carbon 2020, so that the conductivity of the graphite-like carbon 2020 in the thickness direction of the graphite-like carbon 2020 is enhanced, and high ECG signal quality is achieved.

An atomic percentage of a weak carbon-bonding element close to the first surface 1*a* is low, and a first nano-crystal 2021 formed from the weak carbon-bonding element is precipitated in a cluster structure. An atomic percentage of a weak carbon-bonding element closer to the second surface 1*b* is greater, and a first nano-crystal 2021 formed from the weak carbon-bonding element is precipitated in a columnar structure. The atomic percentage of the weak carbon-bonding element is a ratio of a quantity of atoms of the weak carbon-bonding element to a total quantity of atoms in the doped graphite-like carbon film 202. The total quantity of atoms is a sum of a quantity of carbon atoms, the quantity of atoms of the weak carbon-bonding element, and a quantity of atoms of all other elements.

The first nano-crystal 2021 is embedded in the amorphous carbon structure, so that the GLC 2020 may be conductive in the thickness direction of the GLC 2020. However, introduction of the first nano-crystal 2021 reduces density inside the GLC 2020, so that the hardness and the wear resistance of the GLC 2020 are reduced. The second nano-crystal 2022 may be introduced into the GLC 2020, to ensure strength and wear resistance of the GLC 2020.

In an embodiment, the second nano-crystal 2022 is embedded in the amorphous carbon structure of the GLC 2020, so that the hardness and the wear resistance of the GLC 2020 may be enhanced. Specifically, the second nano-crystal 2022 includes a strong carbon-bonding element. The strong carbon-bonding element is an element that has strong affinity with the carbon element and that easily chemically bonds with the carbon element to form a carbide. For example, the strong carbon-bonding element may be Cr, W, or Ti. The second nano-crystal 2022 includes at least one strong carbon-bonding element, that is, the second nano-crystal 2022 may include only the strong carbon-bonding element Cr, W, or Ti, or may include any combination of two or more of the foregoing strong carbon-bonding elements. The strong carbon-bonding element bonds with the carbon element in the GLC 2020 through the chemical bond, to generate second nano-crystals CrC, WC, and TiC. The foregoing three carbides are all hard carbides, and have advantages of high hardness and high wear resistance. The second nano-crystal 2022 is embedded in the amorphous carbon structure of the GLC 2020, to improve the hardness of the doped GLC film 202 and enhance the wear resistance of the doped GLC film 202.

In an embodiment, an atomic percentage of the strong carbon-bonding element gradually decreases in the thickness direction from the first surface 1*a* to the second surface 1*b*. This design may maintain a great atomic percentage of the weak carbon-bonding element close to the second surface 1*b*, so that the doped GLC film 202 maintains high electrical signal quality close to the second surface 1*b*. In addition, from the first surface 1*a* to the second surface 1*b*, the atomic percentage of the strong carbon-bonding element gradually decreases, and the atomic percentage of the weak carbon-bonding element gradually increases. Such a complementary design helps improve bonding force of the doped GLC film 202. The atomic percentage of the strong carbon-bonding element is a ratio of a quantity of atoms of the strong carbon-bonding element to a total quantity of atoms in the doped GLC film 202. The total quantity of atoms is a sum of a quantity of carbon atoms, the quantity of atoms of the strong carbon-bonding element, and a quantity of atoms of all other elements.

In an embodiment, the second nano-crystals 2022 are distributed between cluster structures and columnar structures of a plurality of first nano-crystals 2021. A distribution manner of the second nano-crystals 2022 and the first nano-crystals 2021 helps enhance bonding force inside the doped GLC film 202. In addition, because the second nano-crystal 2022 is a hard carbide, embedding the second nano-crystals 2022 between the cluster structures and the columnar structures of the first nano-crystals 2021 helps better enhance the hardness of the entire doped GLC film 202.

In conclusion, based on the doped GLC film 202 including the GLC 2020, and the first nano-crystals 2021 and the second nano-crystals 2022 that are both embedded in the GLC 2020, not only the conductivity of the doped GLC film 202 in the thickness direction of the doped GLC film 202 but also high hardness and high wear resistance of the entire doped GLC film 202 may be ensured. In this way, the ECG electrode 20 may have a longer service life while ensuring high electrocardiography signal quality. Therefore, user experience is enhanced.

In an embodiment, the ECG electrode 20 further includes a transition layer 203. The transition layer 203 is located between the outer surface of the electrode substrate 201 and the doped GLC film 202. Because the electrode substrate 201 and the doped GLC film 202 are made of different materials, bonding force between the electrode substrate 201 and the doped GLC film 202 is weak. Atoms may be diffused between the transition layer 203 and the electrode substrate 201 and between the transition layer 203 and the doped GLC film 202, to improve the bonding force between the electrode substrate 201 and the doped GLC film 202. Further, to enhance attachment effects of the doped GLC film 202, the transition layer 203 is usually made of a same material as the strong carbon-bonding element, that is, the transition layer 203 includes one or more of the following materials: Cr, W, and Ti. For example, the transition layer 203 may be attached to the outer surface of the electrode substrate 201 in a plating manner such as magnetron sputtering, arc plasma plating, and ion plating. The foregoing plating manner is easy to operate and control and convenient to promote and use.

An embodiment of this disclosure further provides a fabrication method for an ECG electrode 20. The ECG electrode 20 includes an electrode substrate 201 and a doped GLC film 202 located on an outer surface of the electrode substrate 201. The doped GLC film 202 includes GLC 2020, and first nano-crystals 2021 and second nano-crystals 2022 that are doped in the GLC 2020. The GLC 2020 includes a carbon element. The GLC 2020 has an amorphous carbon structure. The first nano-crystal 2021 includes a weak carbon-bonding element. The weak carbon-bonding element has a part that exists in a form of a metallic elementary substance. The first nano-crystal 2021 includes a columnar structure. The columnar structure extends in a thickness direction of the doped GLC film 202. The second nano-crystal 2022 includes a strong carbon-bonding element. The strong carbon-bonding element bonds with the carbon element in the GLC 2020 through a chemical bond. The second nano-crystals 2022 are distributed between adjacent and spaced columnar structures.

In an embodiment, the electrode substrate 201 may be plated in a PVD manner. APVD plating process includes: bombarding a target material by using a high-energy particle, so that atoms in the target material are sputtered out and then deposited on the outer surface of the electrode substrate 201 to form a thin film. The target material is a material with which the outer surface of the electrode substrate 201 is plated. In this embodiment of this disclosure, the target material includes high-purity graphite, the weak carbon-bonding element, or the strong carbon-bonding element, and is used to form the GLC 2020, the first nano-crystal 2021, or the second nano-crystal 2022.

Figure 3:
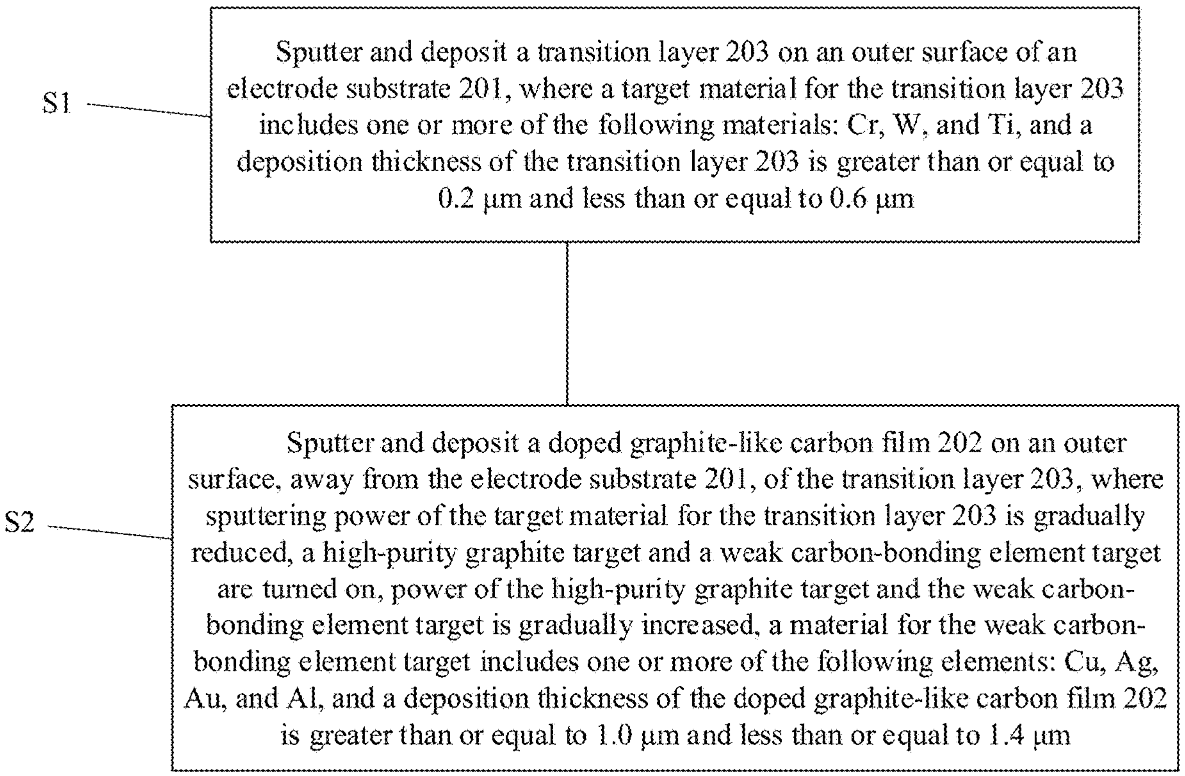
FIG. 3 is a flowchart of a fabrication process of an ECG electrode 20 according to an embodiment of this disclosure.

FIG. 3 is a flowchart of the fabrication method for the ECG electrode 20 according to an embodiment of this disclosure. The fabrication method specifically includes the following steps.

Step S1: Sputter and deposit a transition layer 203 on the outer surface of the electrode substrate 201. The target material for the transition layer 203, that is, the strong carbon-bonding element, includes one or more of the following materials: Cr, W, and Ti. A deposition thickness of the transition layer 203 is greater than or equal to 0.2 m and less than or equal to 0.6 m.

Step S2: Sputter and deposit the doped GLC film 202 on an outer surface, away from the electrode substrate 201, of the transition layer 203. After the transition layer 203 is deposited in step S1, sputtering power of the target material for the transition layer 203 is gradually reduced, a high-purity graphite target and a weak carbon-bonding element target are turned on, and power of the high-purity graphite target and the weak carbon-bonding element target is gradually increased. A material for the weak carbon-bonding element target includes one or more of the following elements: Cu, Ag, Au, and Al. A deposition thickness of the doped GLC film 202 is greater than or equal to 1.0 m and less than or equal to 1.4 m.

In an embodiment, the fabrication method for the ECG electrode 20 includes: first, performing dewaxing and deoiling treatment on a surface of the electrode substrate 201 through ultrasonic cleaning, and then performing cleaning and drying by using propane and alcohol in sequence to obtain a clean surface of the electrode substrate 201; then, controlling pressure inside a vacuum chamber to 0.4 Pa, and performing pre-sputtering cleaning on the clean surface of the electrode substrate 201 by using argon plasma; and after cleaning is completed, performing PVD plating treatment on the electrode substrate 201, where an example in which the transition layer 203 is made of Cr, the weak carbon-bonding element is Ag, and the strong carbon-bonding element is Cr is used. A Cr target is first turned on, sputtering power of the Cr target is adjusted to 30 to 65 W, and deposition is performed for 10 to 20 min to obtain a Cr transition layer 203 with a thickness greater than or equal to 0.2 m and less than or equal to 0.6 m. After the transition layer 203 is deposited, the power of the Cr target is gradually reduced from 30 W to 65 W to 10 W to 35 W, and an Ag target and the high-purity graphite target are turned on. Sputtering power of the Ag target is gradually increased from 20 W to 70 W to 85 W to 150 W, and sputtering power of the high-purity graphite target is gradually increased from 150 W to 250 W to 350 W to 400 W. Finally, the doped GLC film 202 with a thickness greater than or equal to 1.0 m and less than or equal to 1.4 m is obtained.

Table 1 shows a plurality of embodiments of the doped GLC film 202 obtained by changing element types or a quantity of element types of the weak carbon-bonding element, the strong carbon-bonding element, and the transition layer 203, and test data of the doped GLC film 202. The test data includes a direct current offset voltage, composite offset instability and internal noise, hardness, and a wear rate.

It should be noted that, in this embodiment of this disclosure, for a test of electrical signal quality of the ECG electrode 20, refer to the national standard YY/T 0196-2005 Disposable Electrocardiography Electrodes. A test instrument is an electrocardiography electrode performance tester YICE0196, which uses a test circuit that complies with the standard YY/T 0196-2005. In the test, an ambient temperature is 23±5° C., and a relative humidity is 40%10%. In this test, the direct current offset voltage and the composite offset instability and internal noise are selected as indexes for measuring ECG signal quality of a plated metal electrode. For each type of electrodes, at least 25 pairs are tested. A test method is specifically as follows.

For the direct current offset voltage, a loop including two glue-to-glue electrodes and a direct current voltmeter with minimum input impedance of 10 MΩ and resolution of 1 mV or higher is used for measurement. According to performance requirements on electrodes in the national standard, the direct current offset voltage should not be greater than 100 mV after a 1-min stable phase.

For the composite offset instability and internal noise, according to the performance requirements on electrodes in the national standard, a voltage generated in a frequency band of 0.15 Hz to 100 Hz (first-order frequency response) after the 1-min stable phase should not exceed 150 μV (peak-to-peak) within the following 5 min.

In addition, a method for testing hardness and wear resistance of the doped GLC film 202 in the plurality of embodiments is as follows.

The hardness is measured by using a nanoindenter.

For the wear rate, a profile of a wear scar section is measured and plotted by using a step profiler, and a specific wear rate W is calculated: $W=(A\times d)/(P\times L)$, where A indicates an area of the wear scar section, d indicates a reciprocating sliding distance, P indicates a normal load, and L indicates a total stroke in a friction process.

TABLE 1

| Doped graphite-like carbon film | Film layer structure (transition layer/weak carbon-bonding element:strong carbon-bonding element:graphite-like carbon) | Hardness (GPa) | Wear rate ($10^{-16}$ · mm3 · N−1m$^{-1}$) | Direct current offset voltage (mV) | Composite offset instability and internal noise (μV) |
|---|---|---|---|---|---|
| First | Cr/Ag:Cr:GLC | 15 | 2.36 | ≤40 | ≤5 |
| Second | Cr/Cu:Cr:GLC | 12 | 3.98 | ≤83 | ≤130 |
| Third | Cr/Au:Cr:GLC | 11 | 8.88 | ≤30 | ≤5 |
| Fourth | Cr/Al:Cr:GLC | 16 | 7.59 | ≤98 | ≤95 |
| Fifth | Cr/W/Ag:W:GLC | 21 | 1.21 | ≤15 | ≤10 |
| Sixth | Cr/W/Cu:W:GLC | 17 | 1.36 | ≤38 | ≤120 |
| Seventh | Cr/W/Au:W:GLC | 18 | 1.78 | ≤95 | ≤12 |
| Eighth | Cr/W/Al:W:GLC | 18 | 3.65 | ≤70 | ≤136 |
| Ninth | Cr/Ti/Ag:Ti:GLC | 24 | 2.11 | ≤56 | ≤15 |
| Tenth | Cr/Ti/Cu:Ti:GLC | 22 | 3.21 | ≤89 | ≤10 |
| Eleventh | Cr/Ti/Au:Ti:GLC | 18 | 6.33 | ≤23 | ≤16 |
| Twelfth | Cr/Ti/Al:Ti:GLC | 19 | 5.48 | ≤80 | ≤79 |
| Thirteenth | Cr/Ag:Au:Cr:GLC | 11 | 18.6 | ≤15 | ≤10 |
| Fourteenth | Cr/Ag:Cu:Cr:GLC | 9 | 23.3 | ≤60 | ≤70 |
| Fifteenth | Cr/Au:Cu:Cr:GLC | 10 | 22.5 | ≤66 | ≤130 |
| Sixteenth | Cr/GLC | 12 | 12.8 | ≤450 | ≤300 |
| Seventeenth | Cr/Cr:GLC | 17 | 9.63 | ≤300 | ≤180 |
| Eighteenth | Cr/Ag:GLC | 4 | 85.7 | ≤60 | ≤5 |

It may be learned from the data in Table 1 that, compared with the sixteenth and the seventeenth doped GLC films without the weak carbon-bonding element, the direct current offset voltage and the composite offset instability and internal noise are significantly reduced in the first to the fifteenth doped GLC films with the weak carbon-bonding element, which indicates that the first nano-crystal 2021 formed from the weak carbon-bonding element has significant effects on improving the conductivity of the GLC 2020. Compared with the eighteenth doped GLC film without the strong carbon-bonding element, the first to the fifteenth doped GLC films have higher hardness and lower wear rates, which indicates that the second nano-crystal 2022 formed from the strong carbon-bonding element has significant effects on improving the hardness and the wear resistance of the doped GLC film 202.

According to the fabrication method for the ECG electrode provided in this embodiment of this disclosure, as an atomic percentage of the weak carbon-bonding element in the doped GLC film increases, the first nano-crystal formed from the weak carbon-bonding element is first precipitated in a cluster structure until the first nano-crystal of the columnar structure that penetrates the doped GLC film is generated, so that a stable longitudinal conductive channel may be formed in the doped GLC film, to enhance conductivity of the doped GLC film in the thickness direction of the doped GLC film. In addition, the strong carbon-bonding element chemically bonds with the carbon element in the GLC to generate the second nano-crystal, and the second nano-crystal is embedded between the GLC and the first nano-crystal, to improve density and hardness of the doped GLC film and enhance wear resistance. Therefore, embedding the first nano-crystal and the second nano-crystal in the GLC may enhance the conductivity, the hardness, and the wear resistance of the GLC. Therefore, an ECG electrode with both excellent ECG signal quality and high hardness and wear resistance is obtained.

The foregoing embodiments are merely intended for describing the technical solutions of this disclosure other than limiting this disclosure. Although this disclosure is described in detail with reference to the foregoing embodiments, persons skilled in the art should understand that they may still make modifications to the technical solutions described in the foregoing embodiments or make equivalent replacements to some or all technical features thereof, without departing from the scope of the technical solutions of embodiments of this disclosure.

What is claimed is:

1. An electrocardiography (ECG) electrode comprising:
- an electrode substrate comprising an outer surface; and
- a doped graphite-like carbon (GLC) film on the outer surface, wherein the doped GLC film comprises:
  - a GLC comprising a carbon element, wherein the GLC has an amorphous carbon structure;
  - first nano-crystals that are doped in the GLC, wherein the first nano-crystals comprise:
    - a weak carbon-bonding element comprising a first part in a form of a metallic elementary substance; and
    - a first columnar structure that extends in a thickness direction of the doped GLC film;
  - second nano-crystals that are doped in the GLC, wherein the second nano-crystals comprise a strong carbon-bonding element that bonds with the carbon element through a chemical bond, and wherein the second nano-crystals are distributed between a plurality of adjacent and spaced columnar structures,
  - a first surface facing the electrode substrate; and
  - a second surface opposite to the first surface, wherein an atomic percentage of the weak carbon-bonding element gradually increases in a first thickness direction from the first surface to the second surface.

2. The ECG electrode according to claim 1, wherein the metallic elementary substance comprises one of copper (Cu) or silver (Ag).

3. The ECG electrode according to claim 1, wherein the doped GLC film further comprises:
- a first surface facing the electrode substrate;
- a second surface opposite to the first surface;
- a third nano-crystal of the first nano-crystals that is in proximity to the first surface, wherein the third nano-crystal has a cluster structure; and
- a fourth nano-crystal of the first nano-crystals that is in proximity to the second surface, wherein the fourth nano-crystal has a second columnar structure.

4. The ECG electrode according to claim 3, wherein the second nano-crystals are distributed between a plurality of cluster structures and the adjacent and spaced columnar structures.

5. The ECG electrode according to claim 1, wherein the strong carbon-bonding element comprises one of chromium (Cr), tungsten (W), or titanium (Ti).

6. The ECG electrode according to claim 1, wherein an atomic percentage of the strong carbon-bonding element gradually decreases in a first thickness direction from the first surface to the second surface.

7. The ECG electrode according to claim 1, wherein the ECG electrode further comprises a transition layer between the electrode substrate and the doped GLC film.

8. The ECG electrode according to claim 7, wherein the transition layer comprises one of chromium (Cr), tungsten (W), or titanium (Ti).

9. An electronic device comprising:
- one or more processors configured to receive an electrocardiography signal of a monitored object; and
- an electrocardiography (ECG) electrode comprising:
  - an electrode substrate comprising an outer surface; and
  - a doped graphite-like carbon (GLC) film on the outer surface, wherein the doped GLC film comprises:
    - a GLC comprising a carbon element, wherein the GLC has an amorphous carbon structure;
    - first nano-crystals that are doped in the GLC, wherein the first nano-crystals comprise:
      - a weak carbon-bonding element comprising a first part in a form of a metallic elementary substance; and
      - a first columnar structure that extends in a thickness direction of the doped GLC film;
    - second nano-crystals that are doped in the GLC, wherein the second nano-crystals comprise a strong carbon-bonding element that bonds with the carbon element through a chemical bond, and wherein the second nano-crystals are distributed between a plurality of adjacent and spaced columnar structures,
    - a first surface facing the electrode substrate; and
    - a second surface opposite to the first surface, wherein an atomic percentage of the strong carbon-bonding element gradually decreases in a first thickness direction from the first surface to the second surface,
  - wherein the ECG electrode is configured to be in contact with a skin of the monitored object to:
    - obtain the electrocardiography signal; and
    - transmit the electrocardiography signal to the one or more processors.

10. The electronic device according to claim 9, wherein the metallic elementary substance comprises one of copper (Cu), silver (Ag), gold (Au), or aluminum (Al).

11. The electronic device according to claim 9, wherein an atomic percentage of the weak carbon-bonding element gradually increases in a first thickness direction from the first surface to the second surface.

12. The electronic device according to claim 9, wherein the doped GLC film further comprises:
- a first surface facing the electrode substrate;
- a second surface opposite to the first surface;
- a third nano-crystal of the first nano-crystals that is in proximity to the first surface, wherein the third nano-crystal has a cluster structure; and
- a fourth nano-crystal of the first nano-crystals that is in proximity to the second surface, wherein the fourth nano-crystal has a second columnar structure.

13. The electronic device according to claim 12, wherein the second nano-crystals are distributed between a plurality of cluster structures and the adjacent and spaced columnar structures.

14. The electronic device according to claim 9, wherein the strong carbon-bonding element comprises one of chromium (Cr), tungsten (W), or titanium (Ti).

15. The electronic device according to claim 9, wherein the ECG electrode further comprises a transition layer between the electrode substrate and the doped GLC film.

16. The electronic device according to claim 15, wherein the transition layer comprises one of chromium (Cr), tungsten (W), or titanium (Ti).

17. The ECG electrode according to claim 1, wherein the metallic elementary substance comprises one of gold (Au) or aluminum (Al).

18. An electrocardiography (ECG) electrode comprising:
- an electrode substrate comprising an outer surface; and
- a doped graphite-like carbon (GLC) film on the outer surface, wherein the doped GLC film comprises:
  - GLC comprising a carbon element, wherein the GLC has an amorphous carbon structure;
  - first nano-crystals that are doped in the GLC, wherein the first nano-crystals comprise:
    - a weak carbon-bonding element comprising a first part in a form of a metallic elementary substance; and
    - a first columnar structure that extends in a thickness direction of the doped GLC film;
  - second nano-crystals that are doped in the GLC, wherein the second nano-crystals comprise a strong carbon-bonding element that bonds with the carbon element through a chemical bond, and wherein the second nano-crystals are distributed between a plurality of adjacent and spaced columnar structures;
  - a first surface facing the electrode substrate; and
  - a second surface opposite to the first surface, wherein an atomic percentage of the strong carbon-bonding element gradually decreases in a first thickness direction from the first surface to the second surface.

19. The ECG electrode according to claim 18, wherein the doped GLC film further comprises:
- a first surface facing the electrode substrate;
- a second surface opposite to the first surface;
- a third nano-crystal of the first nano-crystals that is in proximity to the first surface, wherein the third nano-crystal has a cluster structure; and
- a fourth nano-crystal of the first nano-crystals that is in proximity to the second surface, wherein the fourth nano-crystal has a second columnar structure.

20. The ECG electrode according to claim 19, wherein the second nano-crystals are distributed between a plurality of cluster structures and the adjacent and spaced columnar structures.

* * * * *